(12) United States Patent
Bischof

(10) Patent No.: US 8,691,246 B2
(45) Date of Patent: Apr. 8, 2014

(54) COMPOSITION FOR FORMING A TEMPORARY INTESTINAL OCCLUSION IN A MAMMAL

(76) Inventor: Georg Bischof, Vienna (AT)

( * ) Notice: Subject to any disclaimer, the term of this patent is extended or adjusted under 35 U.S.C. 154(b) by 27 days.

(21) Appl. No.: 13/547,619

(22) Filed: Jul. 12, 2012

(65) Prior Publication Data

US 2013/0017231 A1    Jan. 17, 2013

Related U.S. Application Data

(60) Provisional application No. 61/602,845, filed on Feb. 24, 2012.

(30) Foreign Application Priority Data

Jul. 13, 2011    (AT) .................................... 1026/2011

(51) Int. Cl.
*A61K 31/718*    (2006.01)
*A61K 9/00*    (2006.01)

(52) U.S. Cl.
USPC .......................................... 424/400; 514/60

(58) Field of Classification Search
USPC ....................................................... 424/400
See application file for complete search history.

(56) References Cited

U.S. PATENT DOCUMENTS

| | | | |
|---|---|---|---|
| 5,129,915 A * | 7/1992 | Cantenys | 606/192 |
| 2004/0180088 A1 * | 9/2004 | Dudhara et al. | 424/471 |
| 2004/0186502 A1 * | 9/2004 | Sampson et al. | 606/191 |
| 2005/0053662 A1 | 3/2005 | Sahatjian et al. | |
| 2006/0034919 A1 * | 2/2006 | Hu et al. | 424/464 |
| 2007/0191768 A1 | 8/2007 | Kolb | |
| 2008/0215036 A1 | 9/2008 | Vogel et al. | |

FOREIGN PATENT DOCUMENTS

| | | |
|---|---|---|
| WO | WO 96/22789 | 8/1996 |
| WO | WO 2008/102341 | 8/2008 |
| WO | WO 2008/103891 | 8/2008 |
| WO | WO 2009/044403 | 4/2009 |
| WO | WO 2009/137446 | 11/2009 |

OTHER PUBLICATIONS

Zainal, "Physicochemical Properties of Carboxy-methylated Sago (Metroxylon sagu) Starch", Journal of Food Science, 70, 2005.*

* cited by examiner

*Primary Examiner* — David J Blanchard
*Assistant Examiner* — John P Nguyen
(74) *Attorney, Agent, or Firm* — Drinker Biddle & Reath LLP

(57) ABSTRACT

A composition for forming a temporary intestinal occlusion in a mammal is flowable and solidifiable to form a solid plug at a predetermined site in the intestine, the structure of the plug being changeable to allow for a subsequent, at least partial removal of the occlusion. The composition is or comprises a flowable solution, suspension, or dispersion in a solvent or mixed solvent, and comprises the following: a) a suspension of a solid in water or an aqueous mixed solvent, the suspension having a water content which exceeds the flow limit of the suspension by a specific amount; b) a dehydrating agent in an amount which is sufficient to bind the specific amount of water, so that, as a consequence of dehydration, the flow limit of the suspension is exceeded; and c) a means for passivating the dehydrating agent.

13 Claims, No Drawings

COMPOSITION FOR FORMING A TEMPORARY INTESTINAL OCCLUSION IN A MAMMAL

This application claims benefit of Austrian Patent Application No. A1026/2011, filed 13 Jul. 2011 in the name of Georg Bischof, and of U.S. provisional patent application No. 61/602,845 filed Feb. 24, 2012 by Georg Bischof. Both of these applications are incorporated herein by reference in their entirety.

The present invention relates to the field of medical endoscopy and endo-surgery, and, more specifically, the field of enteroscopy and entero-surgery.

For many years, endoscopy has been a well-established diagnostic procedure used in human and veterinary medicine. The endoscopes used for this procedure have been undergoing continuous development, and today they do not only allow for the simple illumination or imaging of the interior of the body, e.g. by using optical fibers, but are also equipped for performing minimally invasive surgery. Apart from fiber optics, modern endoscopes comprise, for example, air insufflators or gas pumps, irrigators, aspiration pumps, as well as flexible tools such as cannulae for injections, gripping or cutting tools, or wire electrodes for achieving coagulation by means of electrical current. The endoscope has several channels for introducing the medical tools required for the respective surgical intervention.

Especially in the case of enteroscopic surgical interventions in the intestines of human beings and animals, complications often occur due to feces passing the location which is to be examined and/or to be treated surgically, in spite of previous administrations of laxatives, which does not only make the procedure more difficult and lengthier, but, in the case of surgical interventions, e.g. for obtaining tissue samples or removing tissue, also constitutes a risk of infection for the patient. Thus, it would be desirable to make it possible to seal the intestine for the duration of enteroscopic surgery.

In literature, several solutions for this task can be found. While the main claim of WO 2008/103891 generally covers the formation of a polymer plug "at a site in a mammal" by letting a viscous polymeric composition solidify at body temperature, the only purpose of this application, as described in the rest of the application, consists in the closure of arteries, i.e. in hemostasis. The disclosure therein is based on reversely thermosensitive polymers, i.e. on polymers which are water-soluble at room temperature but precipitate from the solution at body temperature. Examples include poloxamers such as those marketed by BASF under the trade name Pluronics®.

Further examples can be found in WO 2009/137446 A2 and US 2008/215036 A1, which also describe poloxamers. WO 2009/044403 A2 describes compositions containing copolymers of hydroxy fatty acids, which increase their viscosities when contacted with physiological fluids, for tissue repair purposes. And WO 96/22789 A1 discloses biocompatible polymers selected from alginate, chitosan, and poly(L-amino acids) for occluding vessels.

These embodiments, however, have the disadvantage that it is difficult to transport the respective composition to the desired occlusion site within the intestine and to prevent them from at least partially flowing off before a plug has been formed. If the plug is to be formed by swelling, as described in WO 96/22789 A1, for example, it is necessary to pump a relatively large amount of liquid into the intestine, which makes it even more likely that the composition flows off from the desired site of use.

In addition, mechanisms which work in blood vessels, where the respective compositions come into contact with relatively large quantities of liquid, i.e. blood, to achieve a fast change of temperature or viscosity, do not work in the same way in the intestine: prior to intestinal surgery, patients are usually administered laxatives, which means that the composition only comes into contact with small amounts of liquid adhering to the intestinal wall.

Therefore, it was an aim of the present invention to provide a composition with which the above-mentioned disadvantages can be overcome.

DISCLOSURE OF THE INVENTION

This aim is achieved by providing a composition for forming a temporary intestinal occlusion in a mammal, said composition being flowable and suitable to be solidified at a desired site within the intestine to form a solid plug, the structure of which is changeable to allow for a subsequent, at least partial removal of the occlusion, said composition being or comprising a flowable solution, suspension, or dispersion in a solvent or mixed solvent, characterized in that the composition comprises the following:

a) a suspension of a solid in water or an aqueous mixed solvent, having a water content which exceeds the flow limit of the suspension by a specific amount;

b) a dehydrating agent in an amount which is sufficient to bind the specific amount of water, so that, as a consequence of dehydration, the flow limit of the suspension is exceeded; and c) a means for passivating said dehydrating agent.

Such a composition can be used to create a solid plug of the sedimented solid at the desired site in the intestine by removing or deactivating the passivation of the dehydrating agent. The latter then binds at least the specific amount of water which exceeds the flow limit of the suspension of the solid, which results in the solid's sedimentation and solidification and, thus, to an occlusion of the intestine. The principle of the plug formation is not, or not primarily, based on swelling or gelling the solid itself, but relies on a completely different mechanism, namely sedimentation. While, depending on the type of the dehydrating agent, the dehydration may be effected by swelling, as described below, this does not necessarily have to be the case. This means that the total liquid content of the composition may be lower than in most compositions according to the state of the art.

Herein, "suspension" refers to a stable, not spontaneously sedimenting mixture of a solid and water, which, depending on the particle size of the suspended solid, may contain suspending aids. The particle size of the solid in the suspension is not specifically limited and may even be as low as colloidal dimensions, in which case a suspending aid will mostly not be required.

In addition to water, the solvent of the suspension may contain one or several physiologically acceptable organic solvents, which means that it may be an aqueous mixed solvent. Examples of suitable organic solvents include alcohols and glycols, e.g. glycerol or poly(ethylene glycol), ethers, e.g. glycol ethers, and esters, e.g. glycol esters.

In preferred embodiments, the solid concentration of the aqueous suspension is selected to be not more than 5%, more preferably not more than 3% and even more preferably not more than 1% below the flow limit, so that, firstly, only a very low amount of the dehydrating agent and, secondly, a very short period of time are required for solidifying the composition into a plug. Therefore, solidification is accomplished very fast, before the composition flows off from the delivery site. The specific amount of water exceeding the flow limit preferably only amounts to a few grams or to only 1 gram or less. In some embodiments, the specific amount of water will depend on the distance between the application site and the anus, as will be discussed in more detail below.

The suspended solid is not specifically limited, as long as it is capable of forming a suspension with water or an aqueous solvent, which suspension will solidify by sedimentation at a defined concentration. Possible solids include, for example, various natural and artificial polymers such as polysaccharides, granular plastics and mixtures thereof, but also inorganic solids such as mineral solids, especially soft, non-abrasive, fine powders, e.g. chalk and clay minerals. A "solid" herein also refers to a mixture of two or more solids showing corresponding effects.

The suspended solid preferably is or comprises a polysaccharide, more preferably a starch- or cellulose-based polysaccharide, as they are inexpensive and innocuous for the body and form suspensions the characteristics of which can be well controlled. Starch which is not cold-soluble, e.g. granular, native potato starch, tapioca starch, corn starch, wheat starch, or rice starch, is particularly preferred as the solid, as these fine, spherical, non-abrasive natural substances have clearly defined flow limits and, in addition to the above mentioned advantages, are inexpensive and physiologically acceptable.

The dehydrating agent is not subject to any specific limitations and its functions may rely on different physical or chemical mechanisms. The water may, for example, be bound by chemical reactions, e.g. by spontaneous hydrolysis of instable bonds such as ortho-esters or acetals, to which end the suspension and/or the dehydrating agent may contain further reaction partners such as catalysts, e.g. a weak acid or base. These reaction partners should also be innocuous and physiologically acceptable, just like the thus formed reaction products and, in general, all components of the inventive composition. Further examples of water-binding reactions include hydration and swelling of solids, preferably hygroscopic solids; for these reactions, for example, sodium sulfate and other anhydrous inorganic salts as well as organic polymers, which will be discussed in further detail below, may be used.

The dehydrating agent b) may also be a solid tablet or the like which may be transported to the site of use by means of the gripping tool of the endoscope, for example, whereafter the suspension a) is injected onto said tablet via an endoscope channel, which leads to the sedimentation of the solid and, optionally, swelling of the dehydrating agent, so that the plug is formed (see below).

In theory, also a combination of one of the above defined solid suspensions and a mechanically acting dehydrating agent may be used for the purpose of the present invention; it is, for example, possible to use a dehydrating sponge or a ceramic or glass frit, which, again, are separately transported to the desired site in the intestine and contacted there. The passivation is achieved by said separate delivery to the site of use. However, as such solutions of the task of the invention are more cumbersome, they are not preferred.

The dehydrating agent preferably is or comprises a polymer which is swellable in water and which, for example, may be selected from polymers used as disintegration aids or tablet disintegrants, e.g. starch or cellulose or derivatives thereof, alginates, dextrans, cross-linked poly(vinylpyrrolidone), etc. Other examples include so called superabsorbent polymers, i.e. highly water-absorbing polymers, used for various sanitary articles, for example, and including polymers based on acrylonitrile, acrylic acid, acrylamide, or poly(vinyl alcohol), such as polyacrylate/polyacrylamide, ethylene/maleic anhydride or acrylic acid/sodium acrylate copolymers, cross-linked poly(ethylene oxide), etc. More preferably, the dehydrating agent is a polysaccharide, even more preferably starch, particularly sodium carboxymethyl starch, which, again, are innocuous and very inexpensive.

Moreover, upon swelling, the volume of such a starch-based dehydrating agent increases significantly, which leads to an increase of the volume of the plug, which mainly consists of the sedimented solid, even if the ratio of the amounts of the solid suspension and the dehydrating agent is very high; consequently, the plug may easily fill and thus occlude the intestinal lumen. Therefore, it is, again, possible to keep the total amount of liquid in the composition low.

The amount of dehydrating agent used in the composition of the invention is directly related to the concentration of the suspended polymer amount and the suspension's flow limit. At any rate, the amount has to be sufficient to bind the specific amount of water exceeding the concentration at the flow limit. Preferably, it is sufficient to bind 1%, more preferably between 1 and 10%, even more preferably between 1 and 5%, and even more preferably between 1 and 3%, of the water contained in the composition.

The amount of heat usually liberated upon binding the water also has to be taken into consideration, as the solidifying composition should not be excessively heated. However, one may also make specific use of this amount of heat, as will be described in further detail below.

In some preferred embodiments of the invention, at least a portion of the dehydrating agent at the same time constitutes at least a portion of the suspended solid, as will be described in further detail below.

The type of the means for passivating the dehydrating agent is not subject to any specific limitations, as long as it efficiently prevents the dehydrating agent from reacting with the water contained in the suspension. The passivation may, for example, be removed or deactivated only immediately before use of the composition or even only in the intestine. The passivating means may, for example, consist in a chemical modification of the dehydrating agent, e.g. a protecting group, which has to be removed to activate the dehydrating agent and enable it to react with water. A swellable polysaccharide may, for example, be modified with hydrophobic groups which prevent water from accessing the polysaccharide before they are eliminated.

If the dehydrating action of the agent is based on a chemical reaction with water, the passivating means should be deactivatable at least as fast as the activated dehydrating agent reacts with water. The passivated dehydrating agent may be reacted with an additional reactant contained in the suspension, e.g. an acid or a base, in order to be activated.

In preferred embodiments, however, the passivating means is not a chemical modification, but a coating covering the dehydrating agent, which has to be removed for said agent to be activated. It may, for example, be a water-soluble and/or hydrolyzable coating which gradually dissolves when contacted with the aqueous suspension and thus liberates the dehydrating agent. In such cases, the composition preferably is a two-component system, which is only mixed immediately before its use. The heat of solution generated by exothermic solvation and the heating of the composition while being transported through the endoscope channel both accelerate the dissolution of the coating. In addition, the molecules of the coating being dissolved already bind a portion of the water, so that the suspension of the polymer already approaches its flow limit, even before the dehydrating agent is activated. In these cases, the coating, serving as the passivating means, itself also serves as a dehydrating agent of the present invention.

In particularly preferred embodiments, the coating consists of a material which melts at the temperatures prevailing in the intestine; in this context, again, the heating occurring in the endoscope has to be taken into consideration. Particularly if the intended site of the occlusion is far away from the anus, the introduction of the endoscope takes a long time, up to half an hour, for example. As the temperatures in the intestine normally amount to about 37° C., the endoscope may be heated to over 30° C. in the course of its introduction, e.g. to approx. 35° C. For this reason, it is preferred to use a material as the coating material which does not melt at temperatures below 35° C., more preferably not below 35.5° C., even more preferably not below 36° C., even more preferably not below 36.5° C., and, in special cases, even not below approx. 37° C.

The coating material is preferably selected from natural or synthetic waxes and fats, natural waxes and fats being particularly preferred according to the invention as they are well tolerated and their effects are known. Materials which are used for coating suppositories are particularly preferred, e.g. hardened fat having a melting range close to human body temperatures. Examples include hardened fat obtained from palm kernel and coconut fats, consisting mainly of lauric acid, the melting point of which may be precisely controlled by controlling the degree of a subsequent esterification using glycerol, i.e. by controlling the hydroxyl number of the ester thus obtained. Cocoa butter which may have melting ranges between 30 and 38° C. is another preferred example, even more preferably cocoa butter in the β-modification. Hard fat is particularly preferred, as its melting point can be precisely controlled.

In general, the melting point of the respective coating may also be finely adjusted by the average artisan without undue experimentation by producing mixtures of the above mentioned substances with suitable waxes, fats or resins having higher melting points.

If the coating thickness is adequately selected, a complete melting of the coating and, thus, an exposition of the dehydrating agent during its transport through the heated endoscope channel can be prevented. Under suitable pressure conditions, the composition will pass through the endoscope within a few seconds' time, so that a sufficiently thick coating will not have been completely molten. The same principle applies for a water-soluble coating.

Therefore, the coating should be sufficiently thick in order to guarantee a safe transport through the endoscope channel, while, at the same time, allowing for a fast removal within the intestine.

Depending on the way in which the dehydrating agent is passivated, it may also be suspended in the suspension of the solid or it may be vortexed in the composition of the invention right before its use and then be immediately pumped through the endoscope channel. The suspension of the solid and the dehydrating agent then preferably form a suspension which is stable at least for a few minutes, in order to allow for its homogeneous distribution, which is why dehydrating agents having a very small particle size are preferred as is the use of a well-suspendable coating material, if a passivation by means of a coating is provided.

In particularly preferred embodiments, at least a portion of the suspended solid at the same time constitutes at least a portion of the dehydrating agent, as has already been mentioned above. This means that the suspended solid, or a portion thereof, is capable of binding water on its part, as soon as the passivation has been removed. The means for passivating the dehydrating agent may again consist in a coating or a chemical modification of the latter, as described above. However, in these embodiments of the invention, the passivating means preferably consists in a spatially separate provision of the water and the dehydrating agent, in which case they are only mixed in the intestine or immediately prior to delivering the inventive composition into the intestine.

In such embodiments, before use, the composition preferably is a two-component system, comprising a dehydrating agent in a physiologically acceptable solvent, which is preferably essentially anhydrous, but sufficiently water-miscible, as a first component and water or an aqueous mixture as a second component. The two components are mixed immediately before or during their use, thus forming a suspension of the solid serving as a dehydrating agent in a mixed solvent, which also contains water; at the beginning, the water content of said suspension exceeds the flow limit by the specific amount, but gradually approaches said flow limit as a consequence of the reaction of the dehydrating agent, and reaches it after having bound the specific amount of water, whereupon, again, the solid is sedimented.

Particularly if the two components of the two-component system are mixed outside the intestine, which is preferred according to the invention, as only one channel of the endoscope is needed for supplying the composition of the invention to the site of use, the ratio of the components' amounts have to be determined very precisely as a function of the distance between the site of use and the anus. The mixed components have to be transported to the site of use faster than the specific amount of water is bound by the dehydrating agent, in order to prevent sedimentation within the endoscope channel. A specific example of such an embodiment will be described in the exemplary embodiments below.

Particularly if the two components of the two-component system are mixed outside the intestine, which is preferred according to the invention, as only one channel of the endoscope is needed for supplying the composition of the invention to the site of use, the ratio of the components' amounts have to be determined very precisely as a function of the distance between the site of use and the anus. The mixed components have to be transported to the site of use faster than the amount X of water is bound by the dehydrating agent, in order to prevent sedimentation within the endoscope channel. A specific example of such an embodiment will be described in the exemplary embodiments below.

Alternatively, the two components may also be mixed at the site of use, as mentioned above, which either requires two separate endoscope channels or rendering the suspension thixotropic, in order to prevent it from flowing off from the site of use before being contacted with water. It is also possible to passivate a portion of the solid serving as dehydrating agent by coating or chemical modification, in addition to the spatial separation, said coating or modification being then only inactivated within the intestine, for example by melting.

In addition to the above defined components, a composition of the invention may, of course, also comprise any other components, as long as they do not interfere with the invention's mode of action. Examples include suspension aids, viscosity regulators, surfactants, or binding agents in order to improve the plug's adherence to the intestinal wall, derivatives of natural resins, casein, and other animal proteins, for example. Some embodiments of the composition of the invention may further contain foaming agents and foam stabilizers, as the plug may consist of a solid foam in some cases. For this purpose, granules, consisting of the dehydrating agent and one or more foaming agents, may be covered by a wax or similar coating, so that these agents are activated when the coating is molten or dissolved.

In a second aspect, the present invention relates to a method for forming a temporary intestinal occlusion in a mammal using the composition according to the first aspect of the invention, said method comprising:

i) delivering the composition to a predetermined site in the intestine;
ii) removing or deactivating the passivation of the dehydrating agent in order to cause sedimentation to occur and thus solidify the composition at this site to form a solid plug occluding the intestine; and, optionally,
iii) changing the structure of the plug in order to at least partially remove the occlusion;
wherein step iii) may be omitted, if the structure of the plug in the intestine changes of its own volition in the course of time, i.e. without any interference, and the occlusion is at least partially removed this way.

In preferred embodiments of the inventive method, in order to at least partially remove the occlusion, step iii) comprises the supply of additional water to the plug to liquefy it again by lowering the concentration below the flow limit, so that the plug's components may flow off from the site of use.

A possible general approach for producing a composition according to the first aspect of the invention and particularly for determining the proportion of the components is described in a specific, relatively simple example. The average artisan will first select component a), choosing corn starch (as in the exemplary embodiments 1 and 2), for example. The flow limit of a suspension of the available starch powder batch is determined in simple preliminary tests, for example by adding portions of the starch powder to a stirred body of water having a known weight, e.g. adding portions of 0.5 g of starch to 100 g of water. Using corn starch, a value of approx. 42% by weight will be obtained as the flow limit of the aqueous suspension.

Then the average artisan will select a dehydrating agent, e.g. sodium carboxymethyl starch, and determine the amount of water bound by the agent per weight unit, for example by adding 1 g of the dehydrating agent to 10 ml of water, stirring the water for a short time and then filtering the agent off again and weighing the residual water.

The water absorption capacity of the agent will, for example, be determined to amount to approx. 5 g per 1 g carboxymethyl starch.

After that, the average artisan could decide to use a 40% by weight suspension of corn starch in water (i.e. 40 g of starch in 60 g of water) as the solid suspension of the inventive composition. In order to increase the starch concentration from 40 to 42% and thus exceed the flow limit, causing sedimentation of the starch, the dehydrating agent has to bind approx. 5 g of water, since 40 g of starch in 55 g of water correspond to 42.1% by weight.

This means that the amount of dehydrating agent to be added corresponds to the amount capable of binding 5 g of water, which, according to the above-mentioned determination, is 1 g carboxymethyl starch.

Accordingly, the specific amount in this example would be 5 g of water, and the required minimum amount of component b) would be 1 g of carboxymethyl starch.

In the following, the present invention will now be described with reference to specific exemplary embodiments.

EXAMPLES

Example 1

To an aqueous 40% suspension (based on dry matter) of native corn starch, 3% by weight, based on the starch dry matter, of a granular sodium carboxymethyl starch, as commercially available as PRIMOJEL® from DMV Fronterra or ULTRAMYL® from Gustav Parmentier, for example, were added after having been passivated by means of a cocoa butter coating. When the suspension thus prepared was heated to 37° C., it started to solidify at approx. 35° C. to form a solid sediment which had entirely lost its flowability. When water was added, the solid sediment quickly regained its flowability when reaching a concentration below 35%.

Example 2

To an aqueous 40% suspension (based on dry matter) of native corn starch, 3% by weight, based on the starch dry matter, of a granular sodium carboxymethyl starch, which had been passivated by applying a coating of hard fat, were added. Additionally, 1% by weight, based on the starch dry matter, of a suspension stabilizer, namely of cold-soluble, swellable corn starch, was stirred into the suspension. When stored below 30° C., the suspension did not tend to form a sediment. When the suspension was heated to 37° C., it started to solidify at approx. 36° C. to form a solid sediment which had entirely lost its flowability. When water was added, the solid sediment quickly regained its flowability when reaching a concentration below 35%.

Example 3

To an aqueous 38% suspension (based on dry matter) of native potato starch, 3% by weight, based on the starch dry matter, of a granular sodium carboxymethyl starch, which had been passivated by applying a coating of cocoa butter, were added. When the suspension was heated to 37° C., it started to solidify at approx. 35° C. to form a solid sediment which had entirely lost its flowability. When water was added, the solid sediment quickly regained its flowability when reaching a concentration below 35%.

Example 4

An aqueous 38% suspension (based on dry matter) of native potato starch was stirred at 50° C. for 30 minutes and then cooled to 25° C. Then 3% by weight, based on the starch dry matter, of a granular sodium carboxymethyl starch, which had been passivated by applying a coating of cocoa butter, were added. When stored below 30° C., the suspension did not tend to form a sediment. When the suspension was heated to 37° C., it started to solidify at approx. 35° C. to form a solid sediment which had entirely lost its flowability. When water was added, the solid sediment quickly regained its flowability when reaching a concentration below 33%.

Example 5

Via a cannula, the suspension of Example 1 was introduced into an artificial segment of porcine intestine which was stored at 37° C. A solid sediment formed within a short time, completely occluding the segment of the intestine. After 30 minutes, the solid sediment could easily be removed from the segment of the intestine by rinsing with water.

Example 6

100 ml of a suspension of granular sodium carboxymethyl starch, as commercially available as PRIMOJEL® from DMV Fronterra or ULTRAMYL® from Gustav Parmentier, for example, in glycerol, having a viscosity of approx. 1,500 mPa·s is used as component 1 of a two-component system and pumped into a Y-shaped piece via a tubing. Said sodium carboxymethyl starch serves both as suspended solid and as dehydrating agent. 20 ml of water, serving as component 2, are also pumped into said Y-shaped piece via another tubing. Thus, the means for passivating the dehydrating agent consists, on the one hand, in the spatial separation of the two components of the inventive composition, i.e. of the dehydrating agent and the water, and, on the other hand, in the suspension of the former in glycerol which has to mix with the water at first, in order to enable the inventive composition to become effective.

The components 1 and 2 are mixed in the Y-shaped piece, the viscosity of the mixture being significantly lower than that of the glycerol suspension, amounting to approx. 200 mPa·s. This low-viscosity mixture is delivered to the desired site in the intestine within a few seconds' time via the working channel of an endoscope. Within 10 seconds after mixing the two components, the viscosity of the mixture increases very fast as the granules absorb water, whereby the mixture solidifies to form a solid sediment consisting of carboxymethyl starch granules which have greatly expanded due to the water absorption. This sediment forms a plug, which completely occludes the respective segment of the intestine. By simply adding a sufficient amount of water, the solid sediment is liquefied again after the examination has been completed, so that the occlusion is removed.

Thus, the present invention provides compositions for occluding the intestine of a patient in a simple, inexpensive and physiologically innocuous way, in order to be able to carry out medical interventions.

The invention claimed is:

1. A composition for forming a temporary intestinal occlusion in a mammal, said composition being flowable and solidifiable to form a solid plug at a predetermined site in the intestine, the structure of said plug being changeable to allow for a subsequent, at least partial removal of said occlusion, said composition being or comprising a flowable solution, suspension, or dispersion in a solvent or mixed solvent, wherein said composition comprises the following:
    a) a suspension of a solid in water or an aqueous mixed solvent, the suspension having a water content which exceeds the flow limit of the suspension;
    b) a dehydrating agent in an amount which is sufficient to bind water in an amount equal to the amount by which said water content of said suspension exceeds said flow limit of said suspension, so that, as a consequence of dehydration, the flow limit of the suspension is exceeded; and
    c) a means for passivating said dehydrating agent; wherein the suspended solid is selected from starch- or cellulose-based polysaccharides, granular plastics, chalk, clay minerals and other inorganic solids, and wherein said dehydrating agent is selected from water-swellable polysaccharides, hygroscopic anhydrous inorganic salts, and water-absorbing polymers.

2. The composition according to claim 1, wherein the suspended solid is or comprises granular native starch.

3. The composition according to claim 1, wherein the dehydrating agent is or comprises a water-swellable polysaccharide.

4. The composition according to claim 3, wherein said water-swellable polysaccharide is sodium carboxymethyl starch.

5. The composition according to claim 1, wherein at least a portion of the suspended solid at the same time constitutes at least a portion of the dehydrating agent.

6. The composition according to claim 5, wherein, before its use in the intestine, the composition is a two-component system which contains
    i) as a first component, the solid which at the same time acts as dehydrating agent, suspended in a physiologically acceptable solvent or mixed solvent, and
    ii) as a second component, water or an aqueous mixture, the separation of dehydrating agent and water before the composition's use in the intestine constituting the means
    c) for passivating the dehydrating agent.

7. The composition according to claim 1, wherein the passivating means consists in a coating covering said dehydrating agent.

8. The composition according to claim 7, wherein the coating consists of a material which melts at the temperatures prevailing in the intestine.

9. The composition according to claim 8, wherein the coating material does not melt at temperatures below 35° C.

10. The composition according to claim 9, wherein the coating material does not melt at temperatures below 36° C.

11. The composition according to claim 7, wherein the coating material is selected from hard fat and cocoa butter.

12. A method for forming a temporary intestinal occlusion in a mammal, comprising the following:
    i) delivering a composition, comprising
        a) a suspension of a solid in water or an aqueous mixed solvent, the suspension having a water content exceeding the flow limit of the suspension;
        b) a dehydrating agent in an amount which is sufficient to bind water in an amount equal to the amount by which said water content of said suspension exceeds said flow limit of said suspension, so that, as a consequence of dehydration, the flow limit of the suspension is exceeded; and
        c) a means for passivating said dehydrating agent; to a predetermined site in the intestine;
    wherein the suspended solid is selected from starch- or cellulose-based polysaccharides, granular plastics, chalk, clay minerals and other inorganic solids, and wherein said dehydrating agent is selected from water-swellable polysaccharides, hygroscopic anhydrous inorganic salts, and water-absorbing polymers;
    ii) removing or deactivating the passivation of the dehydrating agent in order to cause sedimentation to occur and thus solidify the composition at this site to form a solid plug occluding the intestine; and, optionally,
    iii) changing the structure of the plug in order to at least partially remove the occlusion.

13. The method according to claim 12, comprising, in step iii), delivering water to the solid plug in order to make it flowable again and to at least partially remove the occlusion.

* * * * *